(12) United States Patent
Heuckeroth et al.

(10) Patent No.: US 9,040,306 B2
(45) Date of Patent: May 26, 2015

(54) HIGH-TEMPERATURE FURNACE, USE OF A SPINEL CERAMIC AND METHOD FOR CARRYING OUT T(O)C MEASUREMENTS OF SAMPLES

(71) Applicant: LANXESS Deutschland GmbH, Cologne (DE)

(72) Inventors: Christian Heuckeroth, Wanfried (DE); Rudolf Kreutzer, Langenfeld (DE); Peter Kawulycz, Leverkusen (DE)

(73) Assignee: LANXESS Deutschland GmbH, Cologne (DE)

( * ) Notice: Subject to any disclaimer, the term of this patent is extended or adjusted under 35 U.S.C. 154(b) by 0 days.

(21) Appl. No.: 14/051,639

(22) Filed: Oct. 11, 2013

(65) Prior Publication Data

US 2014/0038304 A1    Feb. 6, 2014

Related U.S. Application Data

(63) Continuation of application No. 13/819,044, filed as application No. PCT/EP2011/064698 on Aug. 26, 2011, now abandoned.

(30) Foreign Application Priority Data

Aug. 27, 2010 (EP) ..................................... 10174403

(51) Int. Cl.
| | |
|---|---|
| *G01N 31/12* | (2006.01) |
| *F27D 11/02* | (2006.01) |
| *C04B 35/443* | (2006.01) |
| *C04B 35/80* | (2006.01) |
| *F27B 17/02* | (2006.01) |
| *F27D 19/00* | (2006.01) |

(52) U.S. Cl.
CPC ............. *G01N 31/12* (2013.01); *Y10T 436/235* (2015.01); *F27B 17/02* (2013.01); *F27D 11/02* (2013.01); *C04B 35/443* (2013.01); *C04B 35/803* (2013.01); *C04B 2235/783* (2013.01); *F27D 2019/0006* (2013.01); *F27D 2019/0012* (2013.01)

(58) Field of Classification Search
CPC ...... G01N 31/005; G01N 31/12; G01N 31/18; G01N 31/1846; F27B 17/02; F27D 11/02; Y10T 436/235
USPC ........... 436/73, 79, 81, 84, 75, 146, 155, 181; 422/78, 80, 94
See application file for complete search history.

(56) References Cited

U.S. PATENT DOCUMENTS

| | | | | |
|---|---|---|---|---|
| 5,332,200 | A | * | 7/1994 | Gorin et al. .................... 266/280 |
| 2005/0208338 | A1 | * | 9/2005 | Fernie et al. ................... 428/701 |
| 2011/0076198 | A1 | * | 3/2011 | Bettmann et al. ............... 422/78 |
| 2014/0004003 | A1 | * | 1/2014 | Inoue et al. ..................... 422/83 |

FOREIGN PATENT DOCUMENTS

CN              201488944 U      5/2010

OTHER PUBLICATIONS

European Standard EN1484, European Committee for Standardization, Brussels, Belgium dated May 1997.
European Search Report from co-pending Application EP10174403.5 dated Feb. 4, 2011, 3 pages.

\* cited by examiner

*Primary Examiner* — Maureen Wallenhorst

(57) ABSTRACT

The present invention relates to a high-temperature furnace for T(O)C measurement of a sample, which has a furnace housing which bounds a vaporization space and has a sample opening for the dropwise introduction of the sample and at least one flushing opening for introduction of a flushing liquid. According to the invention, the furnace housing is lined with a spinel ceramic on an inner side facing the vaporization space. By means of the spinel ceramic, the vaporization space is lined with a material which allows particularly high temperatures within the vaporization space and thus very complete combustion and is at the same time very resistant to temperature changes. This allows cleaning with a flushing liquid at essentially the operating temperature of the vaporization space and removal of deposited salts, in particular recrystallized organic salts, from the vaporization space in the flushing liquid in dissolved or undissolved form. Aging of the high-temperature furnace by deposited salts can thereby be avoided or at least significantly retarded.

19 Claims, No Drawings

HIGH-TEMPERATURE FURNACE, USE OF A SPINEL CERAMIC AND METHOD FOR CARRYING OUT T(O)C MEASUREMENTS OF SAMPLES

This application is a continuation of U.S. patent application Ser. No. 13/819,044, with the same title, which claims the right of priority under 35 U.S.C. §119 (a)-(d) and 35 U.S.C. §365 of International Application No. PCT/EP2011/064698, filed Aug. 26, 2011, which is entitled to the right of priority of European Patent Application Nos. 10174403.5 filed Aug. 27, 2010, the contents of which are hereby incorporated by reference in their entirety.

The present invention relates to a high-temperature furnace by means of which T(O)C measurements on samples can be carried out in order to be able to determine the proportion of oxidizable carbon in wastewater, in particular in accordance with DIN EN 1484. The present invention further relates to a use suitable for this purpose of a spinel ceramic and also a method for carrying out T(O)C measurements on samples.

Particularly in water and wastewater analysis, the proportion of oxidizable carbon in wastewater is determined in accordance with DIN EN 1484 by determining the TOC (total organic carbon) value; depending on the sample, the measured proportion of carbon does not necessarily have to be organically bound ("T(O)C value"). For this purpose, a sample, in particular a liquid sample, is introduced dropwise into a vaporization space in a high-temperature furnace and essentially completely oxidized so that all of the carbon is present as $CO_2$. The concentration of the $CO_2$ formed can be determined over time by means of an NDIR (nondispersive infrared) detector. The resulting integral of the $CO_2$ concentration over time is proportional to the carbon liberated from the sample. To oxidize the sample, the high-temperature reactor is heated to temperatures of from about 700° C. to 1000° C. For this purpose, the vaporization space of the high-temperature reactor is lined with an appropriately heat-resistant oxide ceramic, e.g. $Al_2O_3$. However, it has been found that salts which interfere in the T(O)C measurement are deposited after some time, so that the high-temperature furnace which has been aged by the salt deposits has to be cooled slowly at particular maintenance intervals and cleaned manually before the high-temperature reactor can again be heated slowly to the operating temperature.

It is an object of the invention to indicate measures which make it possible to reduce the extent of aging effects in a high-temperature furnace for T(O)C measurement.

The object is achieved according to the invention by a high-temperature furnace having the features of claim 1, a use having the features of claim 10 and a method for carrying out T(O)C measurements on samples having the features of claim 11. Preferred embodiments of the invention are indicated in the dependent claims.

The inventive high-temperature furnace for T(O)C measurement on a sample has a furnace housing which bounds a vaporization space and has a sample opening for introducing the sample dropwise. According to the invention, the furnace housing is lined with a spinel ceramic on an inside facing the vaporization space. The term vaporization space refers to the entire volume bounded by the furnace housing.

By means of the spinel ceramic, the vaporization space is lined with a material which allows particularly high temperatures within the vaporization space and thus very complete combustion and at the same time is very temperature-change-resistant. This makes it possible to clean the vaporization space by means of a flushing liquid and remove deposited salts, in particular recrystallized inorganic salts, from the vaporization space either dissolved or undissolved in the flushing liquid at essentially the operating temperature. Aging of the high-temperature furnace by deposited salts can thereby be avoided or at least significantly delayed, as a result of which the operating costs over the life of the high-temperature furnace are reduced. Manual cleaning is not necessary. In particular, cleaning of the high-temperature furnace maintained at operating temperature can be provided between two measurements without the in particular continuous T(O)C measurement of samples being significantly delayed. Damage to the spinel ceramic by the impinging flushing liquid can be avoided due to the high temperature-change resistance, so that microcracks in and fatigue of the spinel ceramic are essentially avoided during flushing. Furthermore, an increased corrosion resistance, in particular in the case of alkali-containing slags, is achieved, so that the use range of the high-temperature furnace can be extended to many different, for example particularly alkali-containing, samples. Furthermore, the spinel ceramic does not give an acidic reaction with water, while, for example, an $Al_2O_3$—$SiO_2$ ceramic as conventional ceramic gives an acidic reaction with water. According to the invention, the occurrence of additional acid can therefore be avoided, which, in particular, reduces the burden on analytical instruments. At the same time, the measurement accuracy can be improved since subsequent measurements are not adversely affected by deposited salts. This allows rapid and precise on-line T(O)C measurement, in particular of wastewater as is formed, for example, in the operation of chemical plants. The properties of the spinel ceramic can be adapted according to the particular use by using various powders with different additives in production of the ceramic. Furthermore, different grain sizes and/or grain size distributions can be set for the spinel ceramic. In addition, various activated and/or unactivated phases having appropriately provided composition proportions can be provided, especially as a function of the mixing ratio of the starting materials and/or temperature profiles in the firing process.

For the purposes of the present invention, a spinel ceramic is, in particular, a ceramic material which has the structure of a spinel. A ceramic is a material which, in particular, has been sintered by ignition or firing of finely particulate, inorganic material at elevated temperatures, for example in the range from ≥900° C. to ≤1500° C. Ceramics often have preferred properties in respect of heat resistance, hardness, electrical insulation, chemical resistance, etc. A spinel structure is a cubic structure which can be formed by a compound of the general type $AB_2X_4$, where A and B are, in particular, metallic elements. Here, A can be a divalent metal cation, B a trivalent metal cation and X an oxide. Examples of divalent cations are $Mg^{2+}$, $Fe^{2+}$, $Zn^{2+}$, $Mn^{2+}$, $Cu^{2+}$, $Ni^{2+}$, $Co^{2+}$, while the trivalent cations can, in particular, be formed by $Al^{3+}$, $Fe^{3+}$, $Mn^{3+}$, $Cr^{3+}$, $Fe^{3+}$, $Ga^{3+}$. The cations are, within wide limits, exchangeable. Specific spinels which can be suitable for the purposes of the invention are, in particular, ordinary spinel ($MgAl_2O_4$), zinc spinet ($ZnAl_2O_4$), iron spinel (Fe, Mg)(Al, Fe)$O_4$, chromium spinel (Fe, Mg)(Al, Cr, Fe)$_2O_4$ or nickel spinel ($NiAl_2O_4$). The spinel ceramic according to the invention encompasses materials as described above and also materials which, as mixed spinels, have substituted mixed crystals and also crystals having defects. In addition, the composition can vary within wide limits. As regards ordinary spinel, the invention encompasses, for example, stoichiometric $MgAl_2O_4$ spinels and likewise MgO-rich or $Al_2O_3$-rich spinels.

The furnace housing has at least one flushing opening for introduction of a flushing liquid. The flushing opening can, in particular, be different from the probe opening so that the flushing liquid does not contaminate the path of the probe and possibly falsify a subsequent measurement. For example, the flushing opening is oriented essentially vertically so that the flushing liquid can trickle down in the direction of gravity over the surface of the spinel ceramic facing the vaporization space in order to clean the high-temperature furnace. The at least one flushing opening is preferably aligned essentially horizontally so that the flushing liquid can run along the boundary of the vaporization space over the side of the spinel ceramic facing the vaporization space. The flushing liquid together with the washed-out salts, which can be present in dissolved or undissolved form in the flushing liquid, can be discharged via, in particular, an outlet lower down in the direction of gravity. Flushing liquid remaining in the vaporization space can be vaporized and discharged from the vaporization space in a manner comparable to a sample measurement. Water can be used as flushing liquid. However, it is also possible to use an organic, in particular carbon-containing, solvent as flushing liquid. When the flushing liquid is completely vaporized and removed from the vaporization space can be established by means of the $CO_2$ measurement which is carried out in any case.

The flushing opening is preferably connected to at least one spraying-in nozzle for introducing an aerosol mist as flushing liquid, with the at least one spraying-in nozzle having an inlet direction oriented essentially horizontally. The flushing liquid can in this way be introduced as mist or vapor and be sprayed under an appropriate pressure against the region of the spinel ceramic opposite the flushing opening. The flushing liquid can detach firmly caked salts more easily by means of the impingement pressure on the spinel ceramic which can be achieved in this way. Particular preference is given to a plurality of flushing openings being arranged preferably uniformly in the circumferential direction at essentially the same vertical height.

The spinel ceramic particularly preferably comprises at least one additive selected from among plasticizers, ceramic fibers and further inorganic fillers. Particular preference is given to at least one additive being finely dispersed or distributed in the ceramic. Matching of the spinel ceramic to particular requirements can be achieved in this way.

The addition of a plasticizer, also referred to as water reducer, superplasticizer or dispersant, significantly reduces the make-up water requirement. Owing to the dispersing effect, all particles can be homogeneously wetted on all sides despite a lower water content. The specific use of ceramic fibers enables the ceramic to be optimized in respect of, for example, temperature-change resistance or nature of the surface and be matched to the desired requirements.

Preference is also given to the spinel ceramic having a discontinuous grain size distribution. This further improves the temperature-change resistance or the thermal shock behavior. The temperature-change resistance is of particular importance for flushing of the furnace. For the purposes of the invention, a discontinuous grain size distribution means that the grain size distribution has a gap in a particular grain size range. For example, the spinel ceramic can have 60-65% by mass of coarse grains and 35-40% by mass of fine grains, with the fine grains encompassing grain sizes in the range from $\geq 1$ $\mu m$ to $\leq 74$ $\mu m$ and the coarse grains can comprise grain sizes in the range from $\geq 74$ $\mu m$ to $\leq 700$ $\mu m$ ($\geq$ means greater than or equal to, $\leq$ means less than or equal to).

In particular, the spinel ceramic has pores having a size in the range $\leq 10$ $\mu m$. Such small pores improve the temperature-change resistance further and lead, if crack formation nevertheless occurs, to rounding of the crack tip which leads to a lower stress at the corresponding point. The pores can have, in particular, a size of from $\geq 0.1$ $\mu m$ to $\leq 10$ $\mu m$. As regards the pores, it is also advantageous for the open porosity to be in the range from $\geq 10\%$ by volume to $\leq 30\%$ by volume. Here, the open porosity of the material is the sum of the voids which are connected to one another and to the surroundings and is also referred to as useful porosity. A high temperature-change resistance combined with satisfactory stability is achieved in this way.

In particular, the spinel ceramic is produced as an essentially isostatically pressed shaped part or produced by a plasma coating process. It is possible to apply the spinel ceramic in a plurality of layers to a substrate by means of the plasma coating process in a manner comparable to a rapid prototyping process. This makes it possible to apply the spinel ceramic to a support material which can more easily be installed in order to line the vaporization space. If necessary, a plurality of spinel ceramic layers can be provided on top of one another, so that in the case of a revision, one or more of the upper layers can be separated from an underlying layer in order to be able to provide a uniform unused surface.

The various layers have, in particular, a different composition and/or grain size distribution. In this way, it is possible to ensure sufficient stability in the underlying layers, for example, while the upper layers are matched to the measurement task. Overall, even better matching of the spinel ceramic to the measurement tasks is possible in this way.

The vapor/$CO_2$ mixture which is obtained by vaporization and oxidation from the liquid sample to be measured is generally conveyed directly via an outlet opening located in the furnace housing which bounds the vaporization space to the NDIR (nondispersive infrared) detector by means of which the concentration of the carbon dioxide formed is determined. The spontaneous vaporization of the sample to be measured produces pulsating measurement signals at the detector. This correlates with the dropping-in frequency of the material to be measured at the furnace inlet. The $CO_2$ formed from the sample thus flows frequently, pulsatingly past the NDIR detector. The detector accordingly determines measured values which are not constant but fluctuate greatly, which can cause the measurement accuracy of the measurement system to suffer. To obtain more constant measurement signals, the high-temperature furnace for the T(O)C measurement according to the invention can be modified in such a way that the vapor/$CO_2$ mixture is deflected by structural elements on the path within the vaporization space to the outlet opening. The structural elements can be located unfastened in the vaporization space by being in mutual contact. As an alternative, the structural elements can be installed variably by means of horizontal and/or vertical raised regions in the vaporization space of the high-temperature furnace. The structural elements can be fastened to the interior wall of the vaporization space. As an alternative, the structural elements can also be fastened to one another. Here, different structural elements can be combined with one another. It is also possible for fastened and unfastened structural elements to be combined with one another, both when they have the same shape and when they have different shapes. The interconnected hollow spaces generated by the structural elements act as buffer volumes. As a result, the pressure fluctuations are compensated on the path within the vaporization space via the outlet opening to the NDIR. The structural elements can be, for example, three-dimensional bodies such as spheres, cuboids, rings, cones or cylinders or three-dimensional bodies having any other shape. It is also possible to use other structural elements such as straight or curved plates, struts or other sheet-like elements. The structural elements can consist of different materials. The structural elements preferably consist of spinel ceramic or are coated with this. The structural elements particularly preferably consist of or are coated with the same spinel ceramic as is used for lining the vaporization space of the high-temperature furnace for T(O)C measurement. A further effect of this structural modification is that nonvolatile constituents, generally inorganic salts which are formed in the oxidation of the sample or are present in the sample, are, due to the deflection of the vapor/$CO_2$ mixture, preferably retained in the vaporization space and do not get to the outlet opening and further to the NDIR. This additionally increases the maintenance intervals of the overall analytical apparatus and thus reduces the operating costs.

The invention further relates to the use of a spinel ceramic for lining a vaporization space of a high-temperature furnace for T(O)C measurement of a sample, where the high-temperature furnace is, in particular, configured and embodied as described above. The spinel ceramic is preferably configured and embodied as described above for the high-temperature furnace. The vaporization space is, by means of the spinel ceramic, lined with a material which allows particularly high temperatures within the vaporization space and thus very complete combustion and at the same time is very resistant to temperature changes. This makes it possible to clean the vaporization space with a flushing liquid at essentially the operating temperature and remove deposited salts, in particular recrystallized inorganic salts, from the vaporization space in the flushing liquid either in dissolved or undissolved form. Aging of the high-temperature furnace by deposited salts can thereby be avoided or at least significantly retarded. This exploits the recognition that a spinel ceramic can readily be used not only for handling of liquid metal melts or metal slags, for example as casting mold, but also in analytical apparatuses, for example in T(O)C measurement, where the important aspect is not so much the heat distortion resistance which is otherwise the main consideration but the temperature-change resistance.

T(O)C measurements on samples, in which a high-temperature furnace which has a vaporization space lined with a spinel ceramic is provided. The high-temperature furnace is, in particular, configured and embodied as described above. Furthermore, the vaporization space is heated to operating temperature and a sample is introduced into the vaporization space. In addition, the sample is vaporized and/or oxidized in the vaporization space and the amount of $CO_2$ formed is measured. According to the invention, a flushing liquid is introduced into the vaporization space at essentially the operating temperature in order to remove inorganic salts from the sample which have recrystallized within the vaporization space. The method can, in particular, be configured and embodied as described above for the high-temperature furnace. The vaporization space is, by means of the spinel ceramic, lined with a material which allows particularly high temperatures within the vaporization space and thus very complete combustion and at the same time is very resistant to temperature changes. This makes it possible to clean the vaporization space with a flushing liquid at essentially the operating temperature and remove deposited salts, in particular recrystallized inorganic salts, from the combustion space in the flushing liquid either in dissolved or undissolved form. Aging of the high-temperature furnace by deposited salts can thereby be avoided or at least be significantly retarded.

It is thus possible, according to the invention, to carry out a method for TOC measurement of samples, which comprises the steps of provision of a high-temperature furnace which has a vaporization space lined with a spinel ceramic, heating of the vaporization space to operating temperature, introduction of a sample into the vaporization space, vaporization and/or oxidation of the sample in the vaporization space, measurement of the amount of $CO_2$ formed and introduction of a flushing liquid into the vaporization space at essentially the operating temperature in order to remove inorganic salts from the sample which have recrystallized within the vaporization space.

In particular, the flushing liquid is sprayed into the vaporization space as an aerosol mist. The flushing liquid can in this way be introduced as mist or vapor and be sprayed under an appropriate pressure against the region of the spinel ceramic opposite the flushing opening. The flushing liquid can detach firmly caked salts more easily by means of the impingement pressure on the spinel ceramic which can be achieved in this way. Particular preference is given to a plurality of flushing openings being arranged preferably uniformly in the circumferential direction at essentially the same vertical height.

The vaporization space is preferably dried after the removal of the inorganic salts at essentially the operating temperature and a further sample is then introduced into the vaporization space for T(O)C measurement. Water can be used as flushing liquid. However, it is also possible to use an organic, in particular carbon-containing, solvent as flushing liquid. When the flushing liquid has completely evaporated and been removed from the vaporization space can be established by means of the $CO_2$ measurement which is carried out in any case. Contamination of the T(O)C measurement by residues of the flushing liquid remaining in the vaporization space is thereby avoided.

Particular preference is given to setting an operating temperature $T_O$ such that 500° C.$\leq T_O \leq$2000° C., in particular 800° C.$\leq T_O \leq$1700° C., preferably 1000° C.$\leq T_O \leq$1500° C. and particularly preferably 1200° C.$\leq T_O \leq$1300° C. At such high temperatures, essentially complete oxidation of the carbon can be achieved without risking materials damage in the spinel ceramic as a result of temperature effects. In particular, it is possible to achieve significantly higher temperatures compared to known high-temperature furnaces for T(O)C measurement, so that the use of (ball) catalysts can be reduced or even dispensed with. The operating costs can be reduced further in this way. In addition or as an alternative, the use of catalyst balls can be reduced by means of an internal prescribed, structural gas path.

In particular, the same operating temperature is set as target parameter immediately after introduction of the sample and immediately after introduction of the flushing liquid. The temperature regulation of the high-temperature furnace thus does not have to be carried out differently during normal operation and flushing operation, so that regulation is simplified. At the same time, non-steady-state temperature effects, for example due to thermal conduction, can be avoided or at least significantly reduced since intermediate cooling and heating and waiting until a steady operating state has been reached are avoided.

Furthermore, the stability and temperature-change resistance of the spinel ceramic is due to its chemical constitution. The formulation of the spinel ceramic used can combine the properties of an oxidic ceramic and a nonoxidic ceramic when the ceramic components are appropriately selected. Thus, oxide ceramics are harder, more wear resistant and more heat resistant but also more brittle than cemented hard material. Nonoxide ceramics, for example nitrides, carbides or borides, have a high chemical and thermal stability, hardness and strength compared to oxide ceramics, but this is associated with lower ductility and quite high brittleness due to a higher degree of covalent bonding and lower degree of ionic bonding and thus high bonding energy. It is therefore also possible to choose modified spinel ceramics. Thus, for example in the case of an $MgAl_2O_4$ ceramic, additional alumina or magnesium oxide can be added in order to obtain, for example, an $Al_2O_3$-rich or MgO-rich spinel ceramic.

What is claimed is:

1. A high-temperature furnace for T(O)C measurement on a sample, the furnace comprising a furnace housing which bounds a vaporization space and has a sample opening for introducing the sample into the valorization space, wherein:
   the furnace housing is lined with a spinel ceramic on an inner side facing the vaporization space, and
   the furnace housing has at least one flushing opening configured for introduction of a flushing liquid into the vaporization space at essentially operating temperatures of the furnace.

2. The high-temperature furnace as claimed in claim 1, further comprising at least one spraying-in nozzle at the at least one flushing opening for introducing the flushing liquid as an aerosol mist, where the at least one spraying-in nozzle has an essentially horizontally oriented input direction.

3. The high-temperature furnace as claimed in either claim 1 or 2, wherein the spinel ceramic comprises at least one additive selected from a group that includes plasticizers, ceramic fibers and further inorganic fillers.

4. The high-temperature furnace as claimed in claim 1 or 2, wherein the spinel ceramic has a discontinuous grain size distribution.

5. The high-temperature furnace as claimed in claim 1 or 2, wherein the spinel ceramic has pores having a size less than 10 μm.

6. The high-temperature furnace as claimed in claim 1 or 2, wherein the spinel ceramic has an open porosity in the range from ≥10% by volume to ≤30% by volume.

7. The high-temperature furnace as claimed in claim 1, wherein the spinel ceramic comprises a ceramic produced as an essentially isostatically pressed shaped part or a ceramic produced by a plasma coating process.

8. The high-temperature furnace as claimed in claim 7, wherein the spinel ceramic comprises various layers having a different composition and/or grain size distribution.

9. The high-temperature furnace as claimed in claim 1, further comprising structural elements comprising three-dimensional bodies installed within the furnace housing.

10. A method for lining a vaporization space of a high-temperature furnace as claimed in claim 1 or 2, the method comprising lining the vaporization space with spinel ceramic.

11. A method for carrying out T(O)C measurements on samples in a high temperature furnace as claimed in claim 1, the method comprising:
    heating the vaporization space to operating temperature,
    introducing a sample into the vaporization space,
    vaporizing and/or oxidizing the sample in the vaporization space,
    measuring the amount of $CO_2$ formed, and
    introducing a flushing liquid into the vaporization space at essentially the operating temperature in order to remove inorganic salts from the sample which may have crystallized on surfaces within the vaporization space.

12. The method as claimed in claim 11, wherein introducing the flushing liquid comprises spraying the flushing liquid into the vaporization space as an aerosol mist.

13. The method as claimed in claim 11, further comprising, after removal of any inorganic salts;
    drying the vaporization space essentially at operating temperature and
    subsequently introducing a further sample for T(O)C measurement into the vaporization space.

14. The method as claimed in claim 13, wherein heating the vaporization space to operating temperature comprises heating the vaporization space to a temperature of 500° C. to 2000° C.

15. The method as claimed in claim 13, wherein heating the vaporization space to operating temperature comprises heating the vaporization space to a temperature of 1200° C. to 1300° C.

16. The method as claimed in claim 11, further comprising setting the same operating temperature as a target parameter immediately after introduction of the sample and immediately after introduction of the flushing liquid.

17. The high-temperature furnace according to claim 1, wherein the at least one flushing opening is configured for receiving an injection device for introduction of the flushing liquid into the vaporization space.

18. A high-temperature furnace for T(O)C measurement on a sample, the furnace comprising:
    a furnace housing defining a vaporization space, and comprising a spinel ceramic lining on an inner side of the housing facing the vaporization space;
    a sample opening for introducing a sample into the vaporization space;
    at least one flushing opening for introducing a flushing liquid into the vaporization space; and
    at least one spray nozzle disposed at at least one flushing opening for introducing an aerosol mist of the flushing liquid into the vaporization space.

19. The furnace according to claim 18, wherein the at least one spray nozzle has an essentially horizontally oriented input direction.

* * * * *